United States Patent
Varney et al.

(10) Patent No.: US 9,656,005 B2
(45) Date of Patent: May 23, 2017

(54) NASAL ASPIRATOR

(71) Applicant: DOREL JUVENILE GROUP, INC., Foxboro, MA (US)

(72) Inventors: James R Varney, Maynard, MA (US); Bryan R Hotaling, Harvard, MA (US)

(73) Assignee: Dorel Juvenile Group, Inc., Foxboro, MA (US)

( * ) Notice: Subject to any disclaimer, the term of this patent is extended or adjusted under 35 U.S.C. 154(b) by 405 days.

(21) Appl. No.: 14/203,298

(22) Filed: Mar. 10, 2014

(65) Prior Publication Data
US 2014/0296793 A1 Oct. 2, 2014

Related U.S. Application Data

(60) Provisional application No. 61/806,293, filed on Mar. 28, 2013.

(51) Int. Cl.
*A61M 1/00* (2006.01)
*A61M 39/24* (2006.01)

(52) U.S. Cl.
CPC ........ *A61M 1/0003* (2013.01); *A61M 1/0072* (2014.02); *A61M 1/0031* (2013.01); *A61M 39/24* (2013.01); *A61M 2205/075* (2013.01); *A61M 2210/0618* (2013.01)

(58) Field of Classification Search
CPC .............. A61M 1/0031; A61M 1/0072; A61M 2205/075; A61M 39/24; A61M 2210/0618
See application file for complete search history.

(56) References Cited

U.S. PATENT DOCUMENTS 2,890,699 A 6/1959 Miller
4,226,233 A * 10/1980 Kritzer .............. A61M 16/0006
128/204.18
4,921,488 A 5/1990 Maitz et al.
5,848,993 A * 12/1998 Tanhehco ............. A61M 1/0011
604/212
6,994,087 B1 * 2/2006 Smith ............... A61M 16/0488
128/205.13
2007/0027433 A1 * 2/2007 Garcia ................ A61M 1/0003
604/319

FOREIGN PATENT DOCUMENTS

| CH | 687851 A5 | 3/1997 |
|---|---|---|
| CN | 2693245 | 4/2005 |
| DE | 1853713 U | 6/1962 |
| EP | 0536219 | 9/1996 |
| EP | 0940150 | 9/1999 |
| EP | 1584340 | 10/2005 |
| EP | 2156854 | 2/2010 |
| EP | 2216058 | 8/2010 |
| FR | 2596277 | 3/1986 |
| GB | 2327062 | 1/1999 |
| WO | 9200111 A1 | 1/1992 |
| WO | 2008019271 | 2/2008 |
| WO | 2010018288 | 2/2010 |
| WO | 2010/126586 A1 | 11/2010 |

OTHER PUBLICATIONS

English translation of German Patent No. DE1853713, 8 pages.

* cited by examiner

*Primary Examiner* — Leslie Deak
*Assistant Examiner* — Kai Weng
(74) *Attorney, Agent, or Firm* — Barnes & Thornburg LLP

(57) ABSTRACT

A nasal aspirator is adapted to remove fluid or tissue from a nasal passageway. The aspirator includes an aspirator tube sized to fit in a nasal passageway.

21 Claims, 8 Drawing Sheets

NASAL ASPIRATOR

PRIORITY CLAIM

This application claims priority under 35 U.S.C. §119(e) to U.S. Provisional Application Ser. No. 61/806,293, filed Mar. 28, 2013, which is expressly incorporated by reference herein.

BACKGROUND

The present disclosure relates to an aspirator, and in particular, to a nasal aspirator for moving and collecting materials from a nasal passage by suction. More particularly, the present disclosure relates to a juvenile nasal aspirator.

SUMMARY

A nasal aspirator in accordance with the present disclosure is used to remove fluid or tissue or foreign material from a nasal passageway of a child or other person. The aspirator includes an aspirator tube coupled to a housing formed to include a chamber that can vary in size and shape and receive air and material that passes through the aspirator tube by suction.

In illustrative embodiments, the housing includes a top cover formed to include a central air-discharge port and an offset air-intake port. The upright aspirator tube is retained on the top cover to lie in fluid communication with the air-intake port. The housing further includes an elastic deformable squeeze bulb that cooperates with the top cover to form a variable-size material-collection air chamber located therebetween to communicate with the separate air-discharge and air-intake ports formed in the top cover. A ring-shaped rim is arranged to mate with a circular lower edge of the top cover and a circular upper edge of the squeeze bulb in illustrative embodiments.

An airflow-management unit is located in the air chamber and coupled to the top cover to communicate with both of the air-discharge and air-intake ports formed in the top cover in illustrative embodiments. The airflow-management unit is configured to provide means for discharging air from the air chamber through the air-discharge port and then drawing air and other materials by suction into the air chamber through the separate air-intake port in response to applying a shape-changing squeezing force to the elastic deformable squeeze bulb and then allowing the elastic deformable squeeze bulb to expand to resume its initial undeformed shape. When a free end of the upright aspirator tube is placed in a nasal passageway of a child or other person, nearby fluid, tissue, or foreign material extant in the nasal passageway will be aspirated (i.e., drawn by suction) into the air chamber through the air-intake port formed in the top cover.

In illustrative embodiments, the airflow-management unit includes an umbrella-shaped pressure-relief valve that is positioned to control the flow of air through the air-discharge port formed in the top cover and a duckbill-shaped vacuum-relief valve that is positioned to control the flow of air through the separate air-intake port. The umbrella-shaped pressure-relief valve opens only when a caregiver squeezes the squeeze bulb to increase the pressure of air in the air chamber. The duckbill-shaped vacuum-relief valve opens only when a vacuum is created in the air chamber because the caregiver subsequently released the squeeze bulb to allow the squeeze bulb elastically to return to its initial undeformed shape. Such a vacuum creates enough suction to open the duckbill-shaped vacuum-relief valve and to draw air and nasal-passageway material into the air chamber through the upright aspirator tube and the air-intake port. This process can be repeated multiple times to extract material from the nasal passageway without removing the aspirator tube from the child's nose or discharging any pressurized air into the child's nasal cavity.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which:

FIG. 1A is a reduced-size front elevation view of the nasal aspirator of FIG. 1 and showing the elastic deformable squeeze bulb in a normal undeformed state;

FIG. 6A is a diagrammatic view suggesting that a caregiver can hold the nasal aspirator between the thumb and the index and middle fingers and apply an upward force using the thumb to deform the elastic deformable squeeze bulb to accomplish the nasal passage aspiration result shown diagrammatically in FIG. 8;

DETAILED DESCRIPTION

Figure 1:
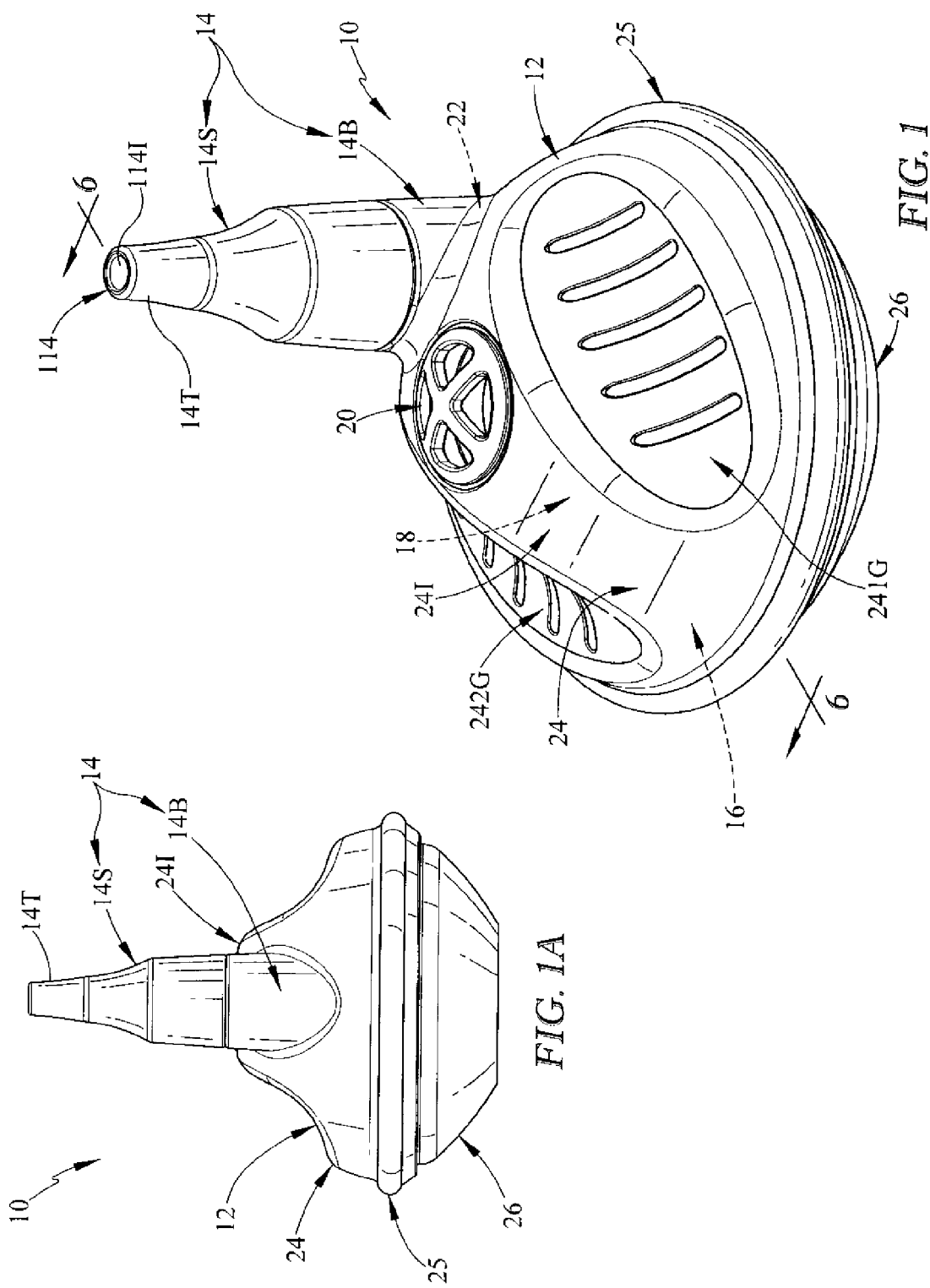
FIG. 1 is a perspective view of a nasal aspirator in accordance with the present disclosure showing that the nasal aspirator includes an upright aspirator tube adapted to be extended into a nasal passageway of a child or other patient and a tube-support housing including a top cover coupled to a base of the upright aspirator tube and formed to support two concave finger grips and to include a central air-discharge port located on a raised island arranged to lie between the two concave finger grips and the upright aspirator tube, a bowl-shaped elastic deformable squeeze bulb located under the top cover and shown in more detail in FIGS. 1A and 2, and a ring-shaped rim arranged to lie between and interconnect the top cover and the squeeze bulb.
Figure 2:
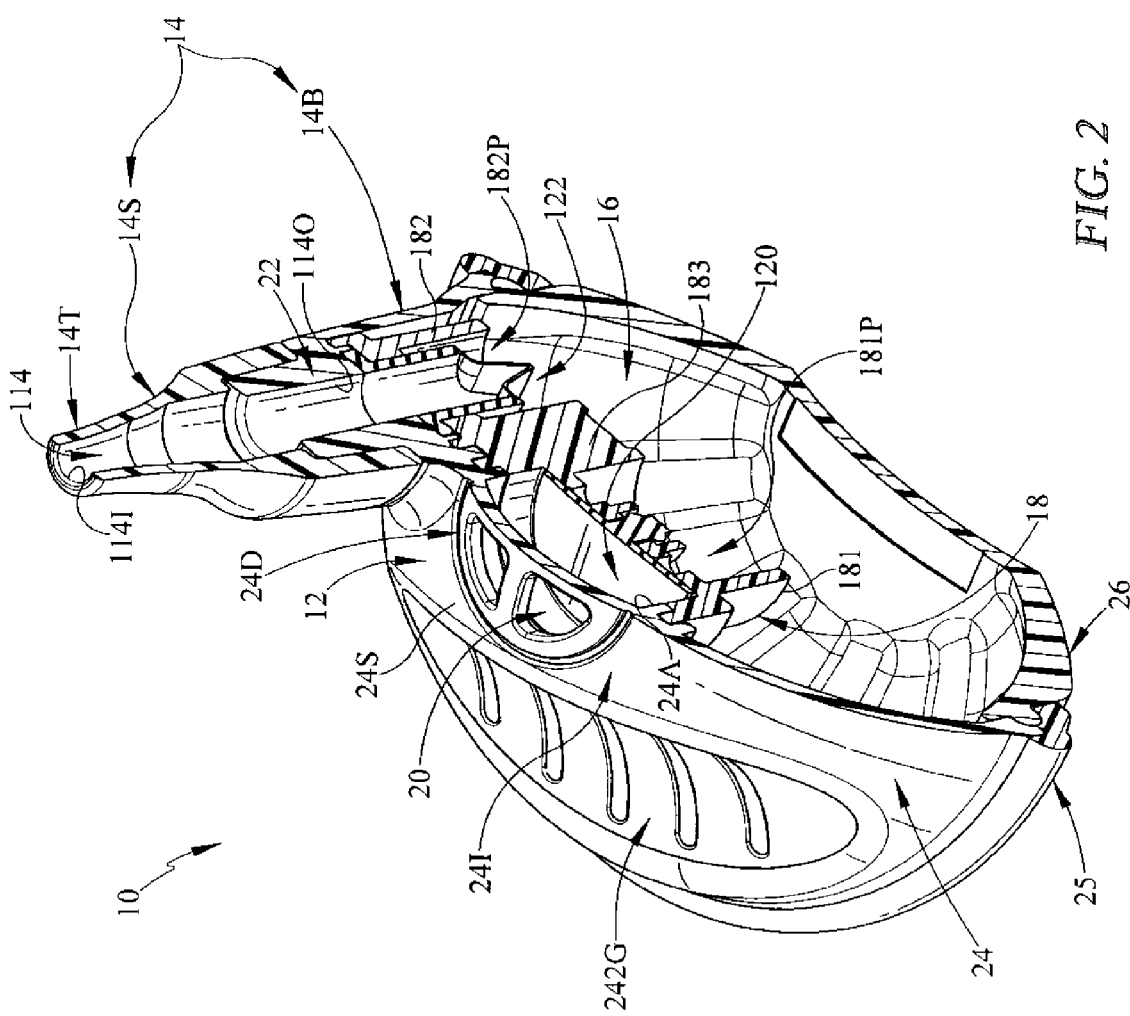
FIG. 2 is a perspective view similar to FIG. 1 with portions broken away to show that the tube-support housing includes an airflow-management unit coupled to an underside of the top cover and configured to provide means for managing the flow of air into and out of the tube-support housing and showing that the airflow-management unit is formed to include a central air exhaust passageway that is aligned in fluid communication with the central air-discharge port and sized to contain an umbrella-shaped pressure-relief valve and an offset air intake passageway that is aligned in fluid communication with the upright aspirator tube and sized to contain a duckbill-shaped vacuum-relief valve, and a variable-sized material-collection air chamber that is filled with air and placed in fluid communication with each of the offset air intake passageway and the central air exhaust passageway of the airflow-management unit.

A nasal aspirator 10 in accordance with the present disclosure includes a tube-support housing 12, an aspirator tube 14 coupled to tube-support housing 12 to communicate with an air chamber 16 provided in tube-support housing 12, and an airflow-management unit 18 located in air chamber 16 as suggested in FIGS. 1 and 2. Airflow-management unit 18 is configured to regulate discharge of air from air chamber 16 through an air-discharge port 20 formed in tube-support housing 12 and intake of air into air chamber 16 through a separate air-intake port 22 formed in tube-support housing 12 so that pressurized air 100 is discharged from air chamber 16 only through air-discharge port 20 to the atmosphere and never through air-intake port 22 and its companion aspirator tube 14 as suggested in FIGS. 7 and 8. In an illustrative embodiment, airflow-management unit 18 includes an umbrella-shaped pressure-relief valve 120 associated with air-discharge port 20 and a duckbill-shaped vacuum-relief valve 122 associated with the separate air-intake port 22 as suggested in FIGS. 3 and 6-8.

Figure 3:
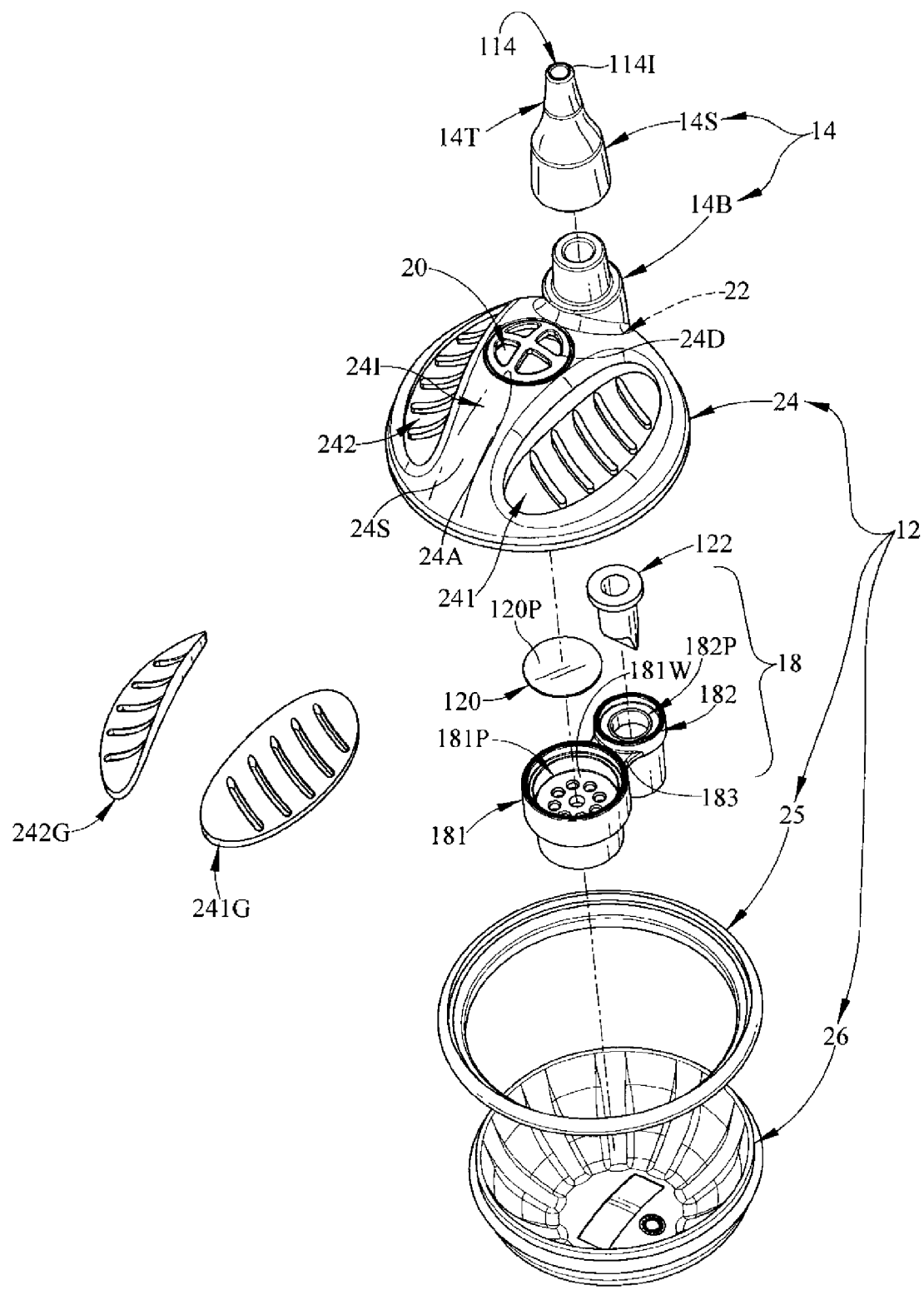
FIG. 3 is an exploded perspective assembly view of the components included in the nasal aspirator of FIGS. 1 and 2 showing, from bottom to top, the bowl-shaped elastic deformable squeeze bulb, the ring-shaped rim, a binoculars-shaped valve housing included in the airflow-management unit and formed to include the central air exhaust passageway (on the left) and the offset air intake passageway (on the right), the umbrella-shaped pressure-relief valve that is included in the airflow-management unit and located above the central air exhaust passageways, the duckbill-shaped vacuum-relief valve that is included in the airflow-management unit and located above the offset air intake passageway, the top cover, first and second concave finger grips shown to the left of the top cover, and an upright aspirator tube comprising a base coupled to the top cover and a sleeve separated from the base and formed to include a narrow tip sized to extend into a nasal passageway of a child or other patient.

Tube-support housing 12 includes a dome-shaped top cover 24, a bowl-shaped elastic deformable squeeze bulb 26 arranged to underlie top cover 24, and a ring-shaped rim 25 as shown, for example, in FIGS. 2 and 3. Rim 25 is arranged to lie between and interconnect top cover 24 and squeeze bulb 26 as suggested in FIG. 2. Top cover 24, squeeze bulb 26, and rim 25 cooperate to form air chamber 16 as suggested in FIGS. 2, 6, and 7.

Fluid, tissue, and foreign material 102 extant in a nasal passageway 200 of a child or other person may be aspirated into air chamber 16 of tube-support housing 12 in the following manner as suggested in FIGS. 6-8. A caregiver first compresses squeeze bulb 26 as suggested diagrammatically in FIG. 7 to pressurize the air in air chamber 16 to a level sufficient to open the normally closed umbrella-shaped pressure-relief valve 120 and discharge pressurized air 100 from air chamber 16 through an air-discharge port 20 that is separate and spaced apart from aspirator tube 14. Then the caregiver releases the squeeze bulb 26 so that the squeeze bulb 26 elastically expands from the deformed state shown diagrammatically in FIG. 7 to a less deformed state shown diagrammatically in FIG. 8 to create a vacuum in air chamber 16 that is sufficient to open the normally closed duckbill vacuum-relief valve 122 and draw by suction air 101 and material 102 from nasal passageway 200 through aspirator tube 14 and airflow-management unit 18 into air chamber 16. This process can be repeated by the caregiver several times in accordance with the present disclosure to extract material 102 from nasal passageway 200 without removing aspirator tube 14 from the nose of a child or other person or causing any pressurized air to be discharged into that nasal passageway 200.

Top cover 24 is formed to include air-discharge port 20 and the separate air-intake port 22 as suggested in FIGS. 1 and 2. Top cover 24 also includes a first cavity 241 sized to receive a concave first finger grip 241G therein and a second cavity 242 sized to receive a concave second finger grip 242G therein as suggested in FIGS. 1 and 3. Finger grips 241G, 242G are arranged to provide a place on top cover 24 for caregivers to place their index and middle fingers when using nasal aspirator 10 so that their thumb can engage the underside of the squeeze bulb 26 as suggested in FIG. 6A. In an illustrative embodiment, aspirator tube 14 is coupled to one side of top cover 24 as suggested in FIGS. 1-3 to provide a raised island 24I in top cover 24 that is located between concave first and second finger grips 241G, 242G and the upright aspirator tube 14 and that is formed to include air-discharge port 20.

In illustrative embodiments, top cover 24 includes a dome-shaped shell 24S coupled to ring-shaped rim 25 and formed to include an aperture 24A in raised island 24I and a round disk 24D arranged to lie in aperture 24A and mate with shell 24S. Disk 24D is formed to include four windows that cooperate to define air-discharge port 20.

Squeeze bulb 26 is bowl-shaped and made of an elastic deformable plastics material in illustrative embodiments of the present disclosure. When exposed to an external deformation force F applied by a caregiver 28 as suggested in FIGS. 6A and 7, squeeze bulb 26 will deform and change shape from a normal expanded state shown, for example, in FIGS. 1A, 2, and 6 to a temporary compressed and deformed state as suggested diagrammatically in FIG. 7 to reduce the volume of the air chamber 16 and force some of the air 100 extant in air chamber 16 past a deflectable pliable elastic pad 120P included in an umbrella-shaped pressure-relief valve 120 included in airflow-management unit 18 and out of the air chamber 16 through air-discharge port 20. No pressurized air is discharged from air chamber 16 through air-intake port 22 and upright aspirator tube 14 owing to the configuration and operation of the normally closed duckbill-shaped vacuum-relief valve 122 included in airflow-management unit 18 and associated with the air-intake port 22 that is coupled to aspirator tube 14.

Figure 7:
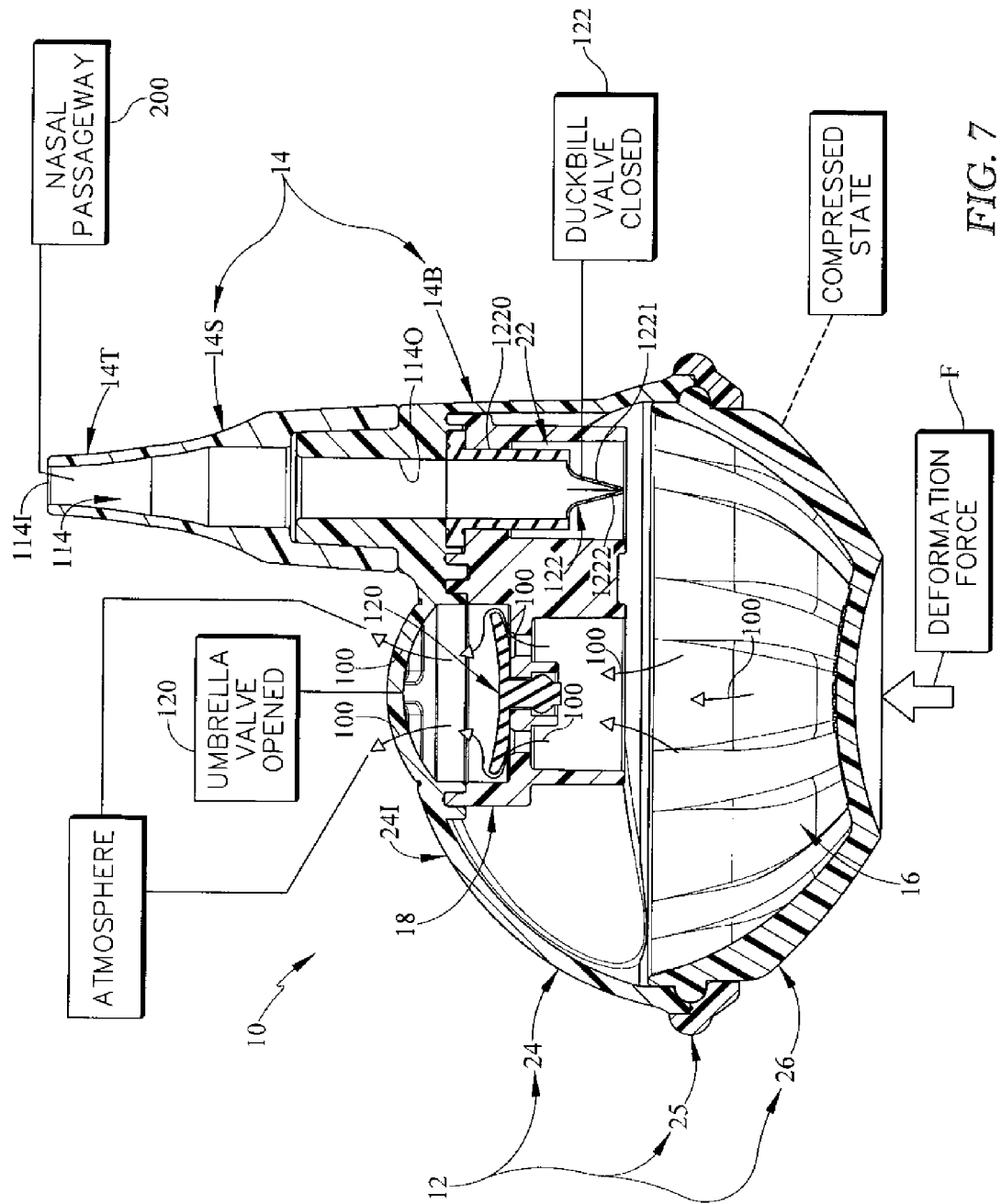
FIG. 7 is a diagrammatic view similar to FIG. 6 suggesting that the elastic deformable squeeze bulb has been pushed upwardly toward the relatively stationary top cover and compressed by a caregiver squeezing the squeeze bulb to assume a deformed shape to reduce the volume of the air chamber and thereby to force air under pressure out of the air chamber past an opened umbrella-shaped pressure-relief valve and through the central air exhaust passageway and the central air-discharge port.
Figure 8:
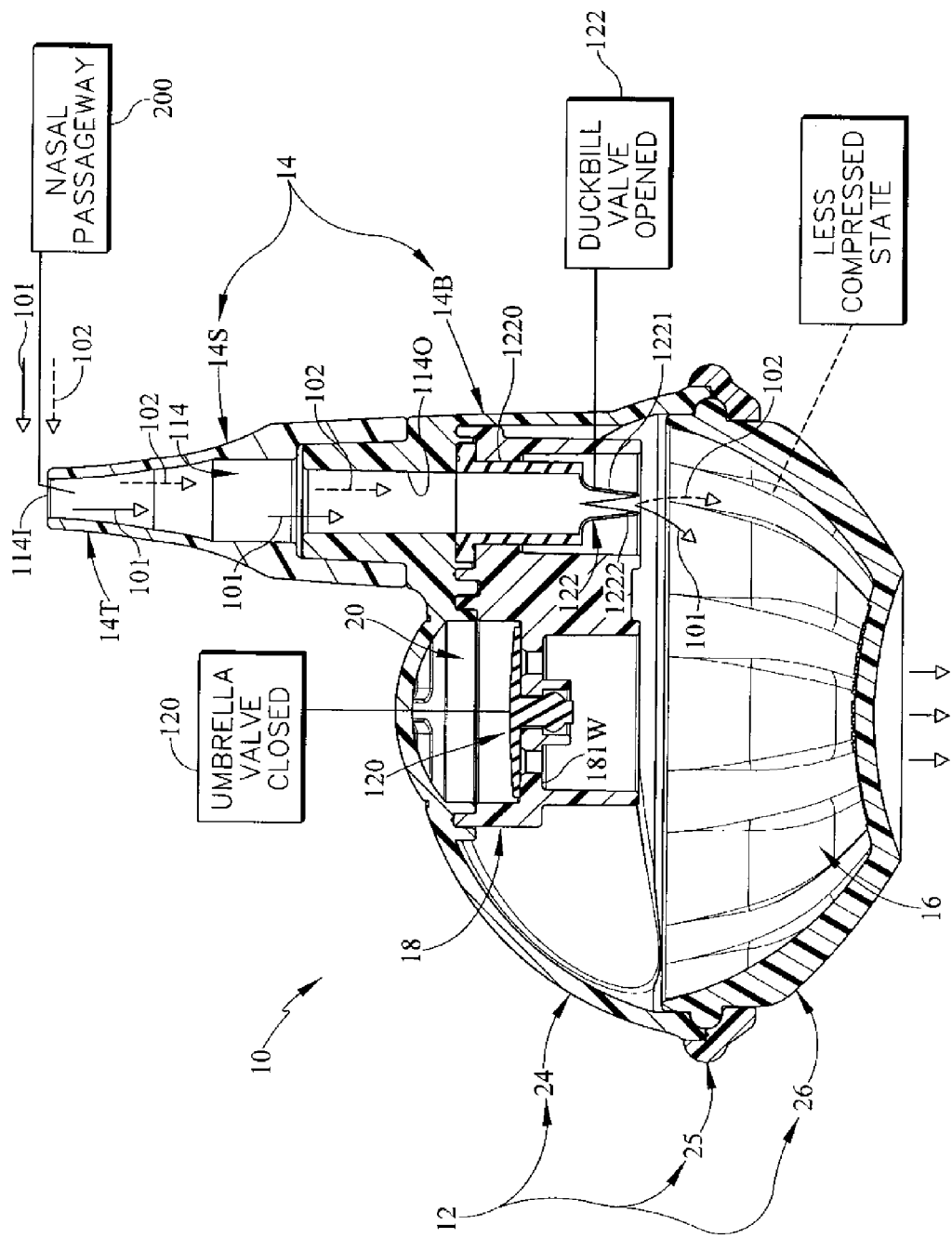
FIG. 8 is a diagrammatic view similar to FIG. 7 suggesting that the squeeze bulb has elastically expanded to assume a less compressed and deformed state once the caregiver releases the squeezing grip on the squeeze bulb so as to create a vacuum in the air chamber that is sufficient to move opposing first and second flaps included in the duckbill-shaped vacuum-relief valve apart to an opened position to couple the air chamber and the outer portion of the air intake passageway in fluid communication so that a vacuum is applied to any fluid, tissue, or body material present in the nasal passageway and such material is drawn by suction into the air chamber (along with air in the nasal passageway) through the air intake passageway and past the opened duckbill-shaped vacuum-relief valve and deposited in the air chamber.

Aspirator tube 14 has a free end that is adapted to be inserted into the nasal passageway 200 of a child or other person as suggested diagrammatically in FIG. 8. Aspirator tube 14 is coupled to one side of top cover 24 of tube-support housing 12 and arranged to extend in an upward direction away from top cover 24 as suggested in FIGS. 1, 1A, and 2. Aspirator tube 14 is aligned with the air-intake port 22 formed in top cover 24 and formed to include a fluid-conducting passageway 114 having an inlet 114I formed in an outer tip 14T of aspirator tube 14 and an outlet 14O opening into air chamber 16 as suggested in FIGS. 2 and 6-8.

In use, aspirator tube 14 of nasal aspirator 10 is placed in the nose of a child or other person to extract fluid. A caregiver places two fingers in finger grips 241G, 242G of aspirator 10 and, with his thumb, applies a compressive force F to squeeze bulb 26 by squeezing his fingers together as suggested in FIG. 6A. In doing the is, the umbrella-shaped pressure-relief valve 120 is opened as suggested in FIG. 7 to allow now pressurized air 100 to exit air chamber 16 while the duckbill-shaped vacuum-relief valve 122 remains closed. As the caregiver releases the compression on the squeeze bulb 26, the umbrella-shaped pressure-relief valve 120 closes and the duckbill-shaped vacuum-relief valve 122 opens owing to development of a vacuum (i.e., negative pressure) in air chamber 16 as suggested in FIG. 8. The vacuum in air chamber 16 is sufficient to cause fluid, tissue, and body material 102 along with air 101 extant in the nasal passageway 200 receiving the top 14T of aspirator tube 14 to be drawn by suction through aspirator tube 14 and the opened duckbill-shaped vacuum-relief valve 122 into air chamber 16 as also suggested in FIG. 8. This process can be repeated multiple times in order to extract material 102 from nasal passageway 200 without receiving the tip 14T of aspirator tube 14 from nasal passageway 200 or discharging any pressurized air exiting air chamber 16 into nasal passageway 200.

Figure 4:
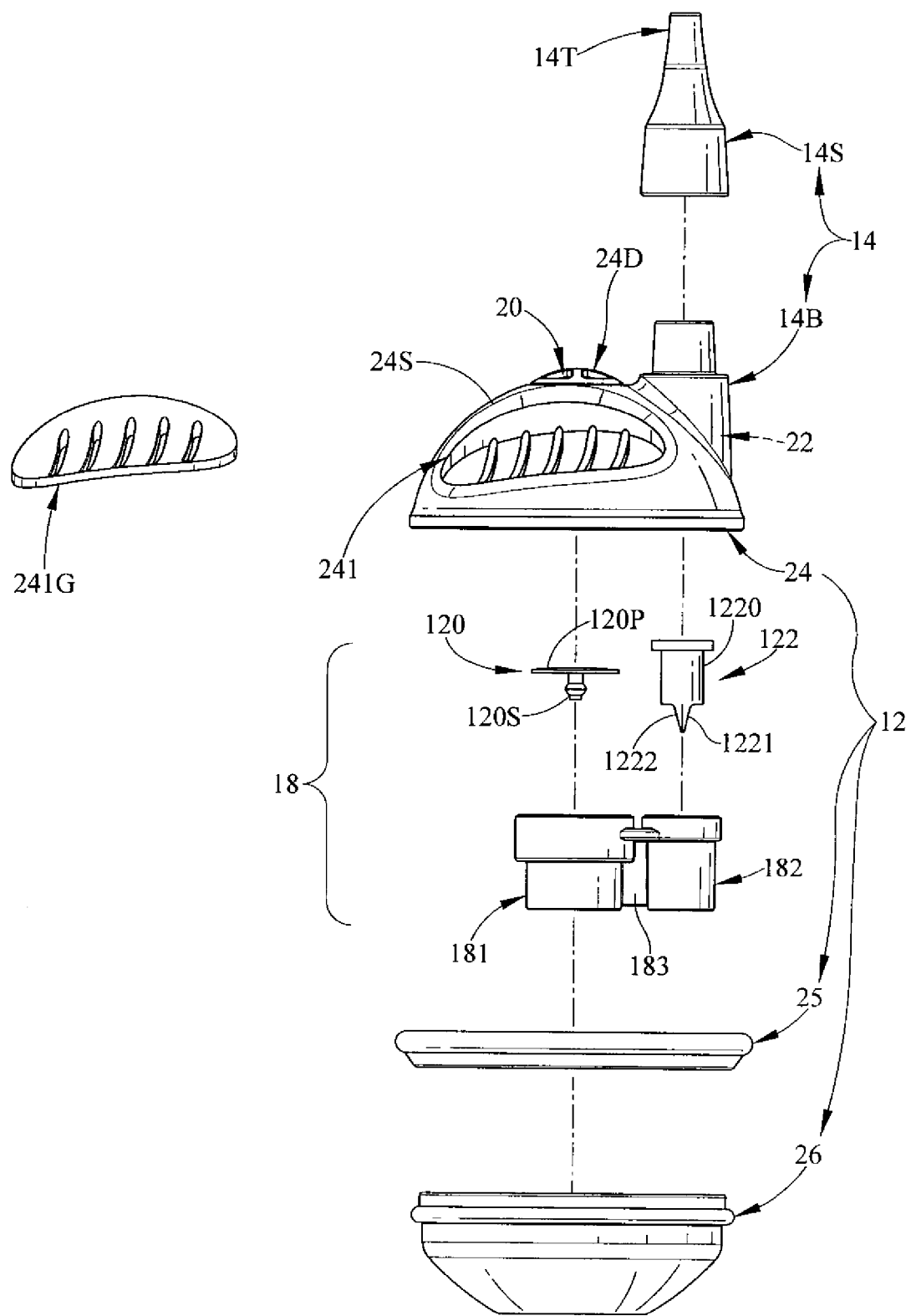
FIG. 4 is a side elevation view of many of the components shown in FIG. 3.
Figure 5:
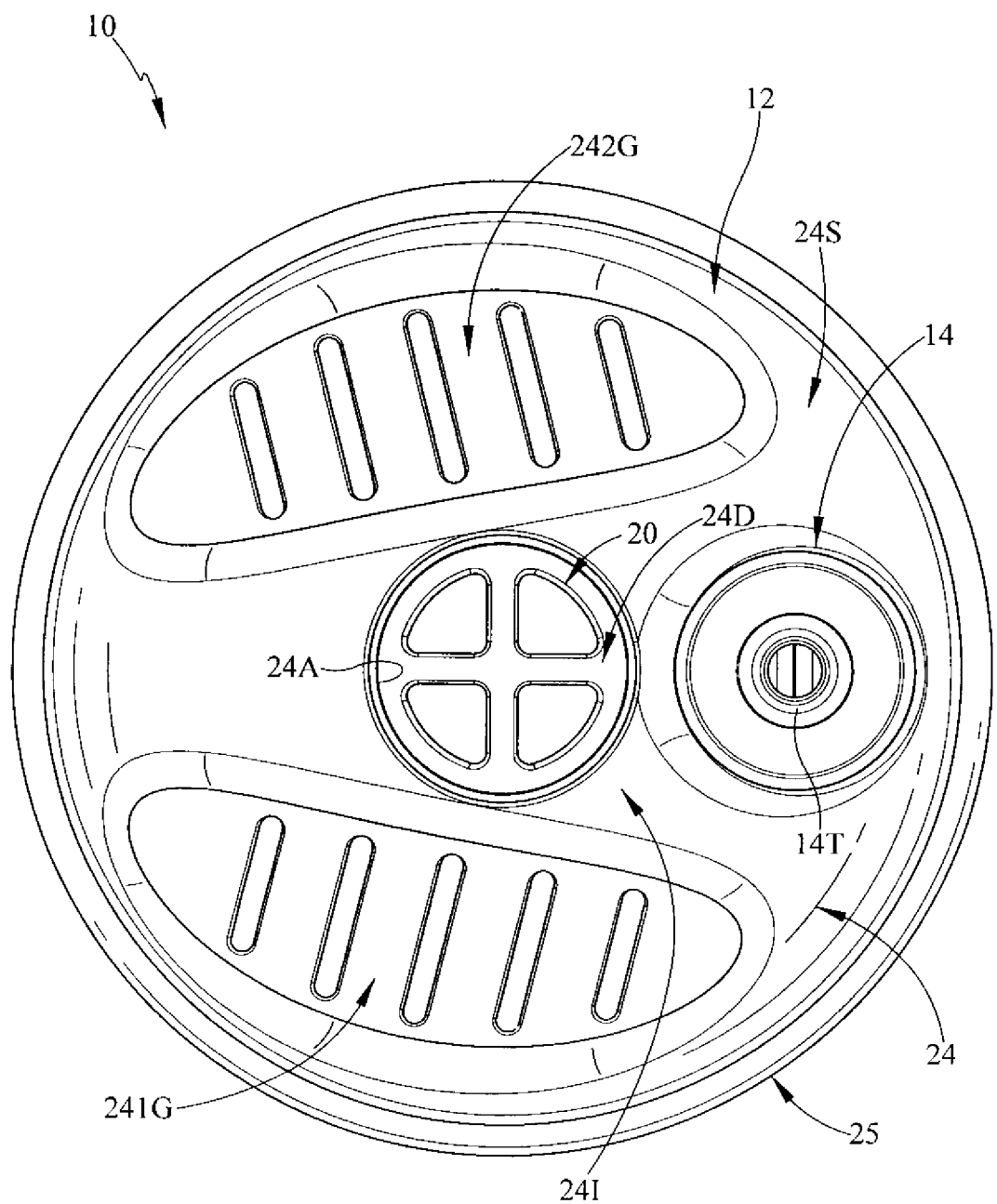
FIG. 5 is an enlarged top plan view of the nasal aspirator of FIG. 1.

Aspirator tube 14 includes a base 14B and a separate sleeve 14S in illustrative embodiments of the present disclosure as suggested in FIGS. 3 and 4. Base 14B is coupled to shell 24S of top cover 24 at air-intake port 22 to form a monolithic component as suggested in FIGS. 1, 1A, 2, 3, and 4. Sleeve 14S is formed to include top 14T and an upper portion of fluid-conducting passageway 114 and is coupled to base 14B. Base 14B is formed to include a lower portion of fluid-conducting passageway 114.

Airflow-management unit 18 includes a binoculars-shaped valve housing 180 including a discharge tube 181, an intake tube 182 coupled to discharge tube 181 and arranged to lie in side-by-side relation, and a tube connector 183 coupled to each of tubes 181, 182 and located between tubes 181, 182 as suggested in FIGS. 3 and 4. Airflow-management unit 18 is coupled to top cover 24 to place discharge tube 181 in alignment and fluid communication with air-discharge port 20 and to place intake tube 182 in alignment and fluid communication with air-intake port 22 as suggested in FIGS. 2 and 6-8. Discharge tube 181 is formed to include a central air exhaust passageway 181P extending therethrough and linking air-discharge port 20 in fluid communication to air chamber 16 as suggested in FIGS. 2 and 6. Intake tube 182 is formed to include an offset air intake passageway 182P extending therethrough and linking air-intake port 22 in fluid communication to air chamber 16.

Figure 6:
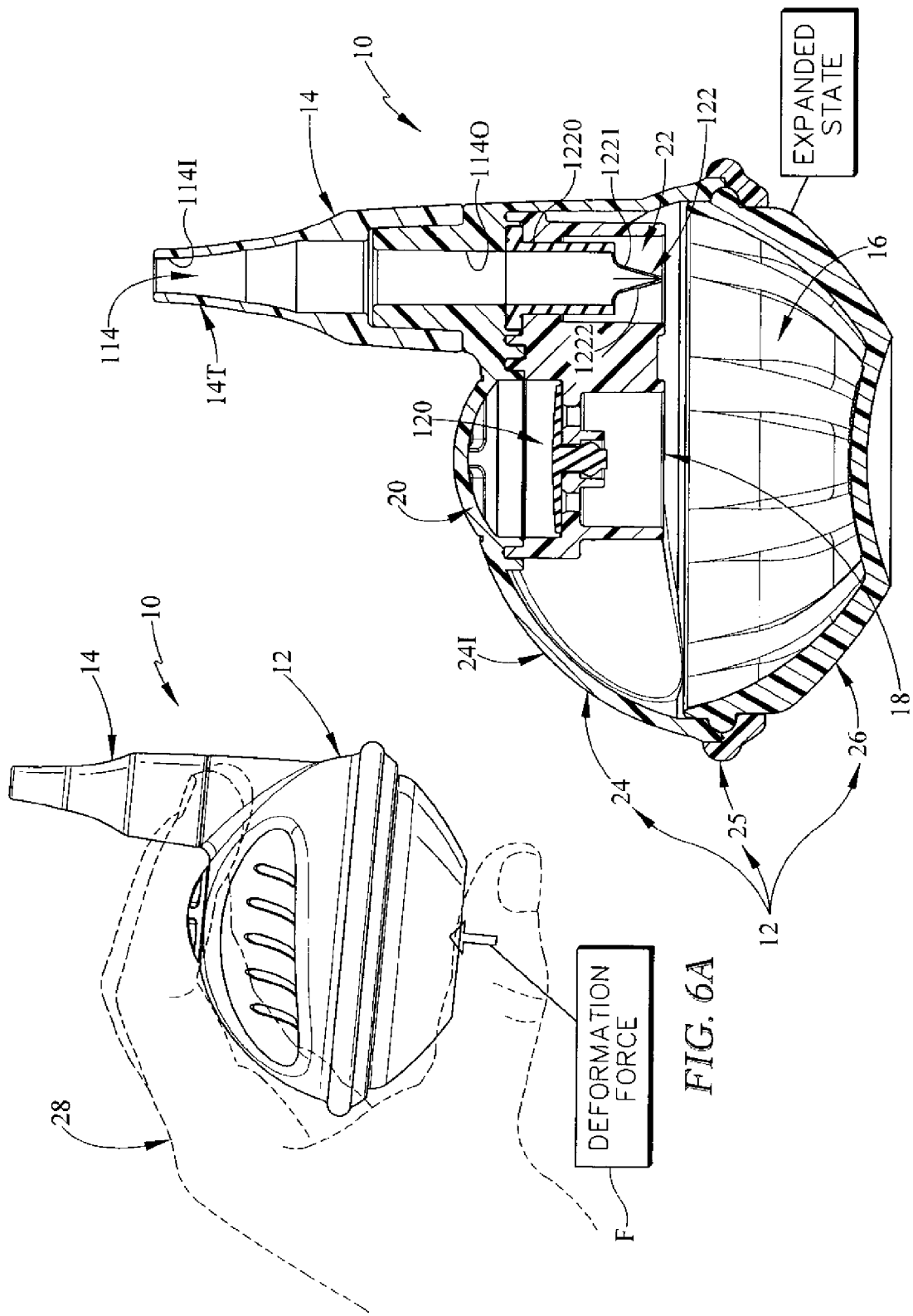
FIG. 6 is an enlarged sectional view taken along line 6-6 of FIG. 1 showing the elastic deformable squeeze bulb in a normal expanded state, the umbrella-shaped pressure-relief valve in a normal closed flow-blocking position arranged to block discharge of air from the variable-size material-collection air chamber bounded by the squeeze bulb, ring-shaped rim, and top cover, and the duckbill-shaped vacuum-relief valve in a normal closed flow-blocking position arranged to block intake of air from the atmosphere into the air chamber through the upright aspirator tube.

Airflow-management unit 18 further includes a pressure-relief valve 120 that is mounted in central air exhaust passageway 181P and configured to be moved automatically from a normally closed position shown in FIG. 6 to a temporarily opened position shown in FIG. 7 whenever the pressure in air chamber 16 exceeds a predetermined pressure level. This elevated pressure level can be achieved by squeezing the squeeze bulb 26 by, for example, applying deformation force F to squeeze bulb 26.

An illustrative pressure-relief valve 120 is umbrella-shaped and includes a stem 120S mounted in a partition wall 181W arranged to partition central air exhaust passageway 181P into upper and lower regions and formed to include a series of apertures linking those regions in fluid communication as suggested in FIGS. 2, 3, 6, and 7. Pressure-relief valve 120 also includes a pliable elastic pad 120P coupled to an upper end of the stem 120S and arranged to lie in the upper region and move from an undeflected position shown in FIG. 6 to a deflected position shown in FIG. 7 when the pressure in air chamber 16 exceeds the predetermined pressure level.

Airflow-management unit 18 also includes a vacuum-relief valve 122 that is mounted in offset air intake passageway 182P and configured to be moved automatically from a normally closed position shown in FIG. 6 to a temporarily opened position shown in FIG. 7 whenever a vacuum (i.e., negative pressure) in air chamber 16 exceeds a predetermined negative pressure level. This negative pressure level can be achieved when a caregiver loosens a squeezing grip applied to squeeze bulb 26 as suggested diagrammatically in FIG. 8.

An illustrative vacuum-relief valve 122 is duckbill-shaped and includes movable first and second flaps 1221, 1222 and a flap anchor 1220 coupled to upper ends of each of flaps 1221, 1222 and mounted to valve housing 180 using any suitable means to cause flaps 1221, 1222 to extend toward air chamber 16 as shown, for example, in FIGS. 2 and 6-8. Vacuum-relief valve 122 is configured to provide means for allowing flow of air and fluid materials in only one downward direction toward air chamber 16 of squeeze bulb 26 when vacuum-relief valve 122 is opened in response to development of a sufficient vacuum in air chamber 16. The flaps 1221, 1222 of duckbill-shaped vacuum-relief valve 122 are biased elastically normally to mate with one another to lie in undeflected closed positions shown in FIG. 6 when there is positive pressure in air chamber 16 and when the vacuum in air chamber 16 is below the predetermined vacuum level. The flaps 1221, 1222 are moved apart automatically to assume deflected opened positions when the vacuum in air chamber 16 exceeds the predetermined vacuum level.

Housing 12 includes a top cover 24 formed to include a central air-discharge port 20 and an offset air-intake port 22. The upright aspirator tube 14 is retained on top cover 24 to lie in fluid communication with air-intake port 22. Housing 12 further includes an elastic deformable squeeze bulb 26 that cooperates with top cover 24 to form a variable-size material-collection air chamber 16 located therebetween to communicate with the separate air-discharge and air-intake ports 20, 22 formed in top cover 24. A ring-shaped rim 25 is arranged to mate with a circular lower edge of top cover 24 and a circular upper edge of squeeze bulb 26 in illustrative embodiments.

An airflow-management unit 18 is located in air chamber 16 and coupled to top cover 24 to communicate with both of the air-discharge and air-intake ports 20, 22 formed in top cover 24 in illustrative embodiments. Airflow-management unit 18 is configured to provide means for discharging air 100 from the air chamber 16 through the air-discharge port 20 and then sucking air 101 into the air chamber 16 through the separate air-intake port 22 in response to applying a shape-changing squeezing force F to the elastic deformable squeeze bulb 26 and then allowing the elastic deformable squeeze bulb 26 to expand to resume its initial undeformed shape. When a free end 14T of upright aspirator tube 14 is placed in a nasal passageway 200 of a child or other person, nearby fluid, tissue, or foreign material 102 extant in the nasal passageway 200 will be aspirated (i.e., drawn by suction) into the air chamber 16 through the air-intake port 22 formed in top cover 24.

Airflow-management unit 18 includes an umbrella-shaped pressure-relief valve 120 that is positioned to control the flow of air through the air-discharge port 20 formed in top cover 24 and a duckbill-shaped vacuum-relief valve 122 that is positioned to control the flow of air through the separate air-intake port 22. The umbrella-shaped pressure-relief valve 120 opens only when a caregiver squeezes the squeeze bulb 26 to increase the pressure of air in the air chamber 16. The duckbill-shaped vacuum-relief valve 122 opens only when a vacuum is created in the air chamber 16 because the caregiver subsequently released the squeeze bulb 26 to allow the squeeze bulb 26 elastically to return to its initial undeformed shape. Such a vacuum creates enough suction to open the duckbill-shaped vacuum-relief valve 122 and draw air 101 and nasal-passageway material 102 into the air chamber 16 through the upright aspirator tube 14 and the air-intake port 22. This process can be repeated multiple times to extract material from the nasal passageway 200 without removing the aspirator tube 14 from the child's nose or discharging any pressurized air into the child's nasal cavity.

Airflow-management unit 18 is coupled to an underside of top cover 24 and configured to provide means for managing the flow of air into and out of tube-support housing 12. Airflow-management unit 18 is formed to include a central air exhaust passageway 181P that is aligned with the central air-discharge port 20 and sized to contain an umbrella-shaped pressure-relief valve 120 and an offset air intake passageway 182P that is aligned with the upright aspirator tube 14 and sized to contain a duckbill-shaped vacuum-relief valve 122. A variable-sized material-collection air chamber 16 is filled with air and placed in fluid communication with each of the offset air intake passageway 182P and the central air exhaust passageway 181P of the airflow-management unit 18.

A caregiver can hold the nasal aspirator 10 between the thumb and the index and middle fingers and apply an upward force F using the thumb as suggested in FIG. 6A to deform the elastic deformable squeeze bulb 26 to accomplish the result shown diagrammatically in FIG. 8. The elastic deformable squeeze bulb 26 has been pushed upwardly toward the top cover 24 as suggested in FIG. 7 to assume a compressed and deformed shape to reduce the volume of the air chamber 16 and thereby to force air 100 out of air chamber 16 past an opened umbrella-shaped pressure-relief valve 120 and through the central air exhaust passageway 181P and the central air-discharge port 20. Then the squeeze bulb 26 is released and allowed to expand to a less compressed state so as to create a vacuum in the air chamber 16 that is sufficient to move opposing first and second flaps 1221, 1222 included in the duckbill-shaped vacuum-relief valve 122 apart to an opened position to couple the air chamber 16 and the outer portion of the air intake passageway 182P in fluid communication so that a vacuum is applied to any air 101 and fluid, tissue, or body material 102 present in the nasal passageway 200 and such air 101 and material 102 are drawn into the air chamber 16 through the air intake passageway 182P and past the opened duckbill-shaped vacuum-relief valve 122 and deposited in the air chamber 16.

The invention claimed is:

1. A nasal aspirator adapted to remove fluid or tissue or foreign material from a nasal passageway of a person, the nasal aspirator comprising
    an aspirator tube sized to be inserted into the nasal cavity of a person,
    a housing coupled to the aspirator tube, the housing including a top cover and an elastic deformable squeeze bulb that cooperates with the top cover to form a variable-size material-collection air chamber located therebetween, the top cover formed to include an air-discharge port in fluid communication with the variable-size material-collection air chamber and an offset air-intake port in fluid communication with the aspirator tube, and
    an airflow-management unit coupled to the top cover of the housing to communicate with both of the air-discharge and the offset air-intake ports formed in the top cover, the airflow-management unit comprising means for discharging air from the air chamber through the air-discharge port and then drawing air and other materials by suction into the air chamber through the offset air-intake port in response to applying a shape-changing squeezing force to the elastic deformable squeeze bulb and then allowing the elastic deformable squeeze bulb to expand to resume its initial undeformed shape so that when a free end of the upright aspirator tube is placed in the nasal passageway of the person, nearby fluid, tissue, or foreign material extant in the nasal passageway will be drawn by suction into the air chamber through the aspirator tube and the air-intake port formed in the top cover of the housing, wherein the airflow-management unit is located entirely within the air chamber.

2. The nasal aspirator of claim 1, wherein the airflow management unit includes a pressure-relief valve that is positioned to control the flow of air through the air-discharge port formed in the top cover and a vacuum-relief valve that is positioned to control the flow of air through the offset air-intake port formed in the top cover, the pressure-relief valve opens only when the pressure of air in the air chamber is increased in response the shape-changing squeezing force being applied to the elastic deformable squeeze bulb, and the vacuum-relief valve opens only when a vacuum is created in the air chamber in response to the squeeze bulb elastically to returning to its initial undeformed shape.

3. The nasal aspirator of claim 2, wherein the airflow management unit includes a discharge tube that forms an air exhaust passageway that extends from the air-discharge port into the air chamber and a partition wall arranged in the air exhaust passageway to divide the air exhaust passageway into upper and lower regions, the partition wall is formed to include a series of apertures linking the upper and lower regions in fluid communication, and the pressure-relief valve moves from an undeflected position arranged to block the passage of air through the series of apertures when the pressure in the air chamber is below a predetermined pressure level to a deflected position arranged to allow the passage of air through the series of apertures when the pressure in the air chamber exceeds the predetermined pressure level.

4. The nasal aspirator of claim 3, wherein the pressure-relief valve includes a stem and a pliable elastic pad coupled to the stem so that the pressure-relief valve is umbrella-shaped, the stem is received in the partition wall to couple the pressure-relief valve to the partition wall, and the pliable elastic pad moves from the undeflected position arranged to block the passage of air through the series of apertures when the pressure in the air chamber is below the predetermined pressure level to the deflected position arranged to allow the passage of air through the series of apertures when the pressure in the air chamber exceeds the predetermined pressure level.

5. The nasal aspirator of claim 2, wherein the vacuum-relief valve is duckbill-shaped and includes a movable first flap, a movable second flap, and a flap anchor coupled to upper ends of each of the movable first and second flaps, the movable first and second flaps of the duckbill-shaped vacuum-relief valve are biased elastically normally to mate with one another to lie in undeflected closed positions when there is positive pressure in the air chamber and when the vacuum in the air chamber is below a predetermined vacuum level, and the movable first and second flaps are moved apart automatically to assume deflected opened positions when the vacuum in the air chamber exceeds the predetermined vacuum level.

6. The nasal aspirator of claim 2, wherein the airflow-management unit includes a binoculars-shaped valve housing including a discharge tube, an intake tube coupled to the discharge tube and arranged to lie in side-by-side relation relative to the discharge tube, and a tube connector coupled to each of tubes and located between the discharge tube and the intake tube.

7. The nasal aspirator of claim 6, wherein the airflow-management unit is coupled to the top cover of the housing to place the discharge tube of the binoculars-shaped valve housing in alignment and fluid communication with the air-discharge port and to place the intake tube of the binoculars-shaped valve housing in alignment and fluid communication with the offset air-intake port.

8. The nasal aspirator of claim 1, wherein the top cover also includes a first cavity sized to receive a concave first finger grip therein and a second cavity sized to receive a concave second finger grip therein, the finger grips are arranged to provide a place on the top cover for caregivers to place their index and middle fingers when using the nasal aspirator so that their thumb can engage the underside of the squeeze bulb.

9. The nasal aspirator of claim 8, wherein the aspirator tube is coupled to one side of the top cover between the concave first and second finger grips received in the top cover so that the aspirator tube is arranged between the index and middle fingers of a caregiver when the nasal aspirator is used.

10. The nasal aspirator of claim 8, wherein the air-discharge port is formed between the concave first and second finger grips received in the top cover so that the air-discharge port is uncovered and arranged between the index and middle fingers of a caregiver when the nasal aspirator is used.

11. A nasal aspirator comprising
an aspirator tube sized to be inserted into the nasal cavity of a person,
a housing coupled to the aspirator tube, the housing including a top cover and an elastic deformable squeeze bulb that cooperates with the top cover to form a variable-size material-collection air chamber located therebetween, the top cover formed to include an air-discharge port in fluid communication with the variable-size material-collection air chamber and an offset air-intake port in fluid communication with the aspirator tube, and
an airflow-management unit including a pressure-relief valve that is positioned to control the flow of air through the air-discharge port formed in the top cover and a vacuum-relief valve that is positioned to control the flow of air through the offset air-intake port formed in the top cover, the pressure-relief valve opens only when a predetermined pressure level is reached in the air chamber, and the vacuum-relief valve opens only when a predetermined level of vacuum is reached in the air chamber,
wherein the airflow management unit includes a discharge tube that forms an air exhaust passageway that extends from the air-discharge port into the air chamber and a partition wall arranged in the air exhaust passageway to divide the air exhaust passageway into upper and lower regions, the partition wall is formed to include a series of apertures linking the upper and lower regions in fluid communication, and the pressure-relief valve moves from an undeflected position arranged to block the passage of air through the series of apertures when the pressure in the air chamber is below the predetermined pressure level to a deflected position arranged to allow the passage of air through the series of apertures when the pressure in the air chamber exceeds the predetermined pressure level.

12. The nasal aspirator of claim 11, wherein the pressure-relief valve includes a stem and a pliable elastic pad coupled to the stem so that the pressure-relief valve is umbrella-shaped, the stem is received in the partition wall to couple the pressure-relief valve to the partition wall, and the pliable elastic pad moves from the undeflected position arranged to block the passage of air through the series of apertures when the pressure in the air chamber is below the predetermined pressure level to the deflected position arranged to allow the passage of air through the series of apertures when the pressure in the air chamber exceeds the predetermined pressure level.

13. The nasal aspirator of claim 11, wherein the vacuum-relief valve is duckbill-shaped and includes a movable first flap, a movable second flap, and a flap anchor coupled to upper ends of each of the movable first and second flaps, the movable first and second flaps of the duckbill-shaped vacuum-relief valve are biased elastically normally to mate with one another to lie in undeflected closed positions when there is positive pressure in the air chamber and when the vacuum in the air chamber is below the predetermined vacuum level, and the movable first and second flaps are moved apart automatically to assume deflected opened positions when the vacuum the in air chamber exceeds the predetermined vacuum level.

14. The nasal aspirator of claim 11, wherein the airflow-management unit includes a valve housing coupled to the top cover of the housing that positions the pressure-relief valve and the vacuum-relief valve relative to the air-discharge port and offset air-intake port formed in the top cover.

15. The nasal aspirator of claim 14, wherein the valve housing includes a discharge tube in fluid communication with the air-discharge port that receives the pressure-relief valve and an intake tube in fluid communication with the offset air-intake port that receives the vacuum-relief valve.

16. The nasal aspirator of claim 15, wherein the valve housing is binoculars-shaped and includes a tube connector that extends between the discharge tube and the intake tube so that the discharge tube and the intake tube are arranged to lie in side-by-side relation relative to one another.

17. A nasal aspirator comprising
an aspirator tube sized to be inserted into the nasal cavity of a person,
a housing coupled to the aspirator tube, the housing including a top cover and an elastic deformable squeeze bulb that cooperates with the top cover to form a variable-size material-collection air chamber located therebetween, the top cover formed to include an air-discharge port in fluid communication with the variable-size material-collection air chamber and an offset air-intake port in fluid communication with the aspirator tube, and
an airflow-management unit including a pressure-relief valve that opens only when a predetermined pressure level is reached in the air chamber, a vacuum-relief valve that opens only when a predetermined vacuum level is reached in the air chamber, and a binoculars-shaped valve housing coupled to the top cover of the housing that receives the pressure-relief valve and the vacuum-relief valve,
wherein the binoculars-shaped valve housing is shaped to position the pressure-relief valve to control the flow of air through the air-discharge port and the binoculars-shaped valve housing is shaped to position the vacuum-relief valve to control the flow of air through the offset air-intake port formed in the top cover.

18. The nasal aspirator of claim 17, wherein the binoculars-shaped valve housing includes a discharge tube, an intake tube coupled to the discharge tube and arranged to lie in side-by-side relation relative to the discharge tube, and a tube connector coupled to each of tubes and located between the discharge tube and the intake tube.

19. The nasal aspirator of claim 18, wherein the discharge tube forms an air exhaust passageway that extends from the air-discharge port into the air chamber, a partition wall is arranged in the air exhaust passageway to divide the air exhaust passageway into upper and lower regions, the partition wall is formed to include a series of apertures linking the upper and lower regions in fluid communication, and the pressure-relief valve moves relative to the partition wall to block or allow the passage of air through the series of apertures.

20. The nasal aspirator of claim 19, wherein the pressure-relief valve includes a stem and a pliable elastic pad coupled to the stem so that the pressure-relief valve is umbrella-shaped, the stem is received in the partition wall to couple the pressure-relief valve to the partition wall, and the pliable elastic pad moves from an undeflected position arranged to block the passage of air through the series of apertures when the pressure in the air chamber is below the predetermined pressure level to a deflected position arranged to allow the passage of air through the series of apertures when the pressure in the air chamber exceeds the predetermined pressure level.

21. The nasal aspirator of claim 17, wherein the vacuum-relief valve is duckbill-shaped and includes a movable first flap, a movable second flap, and a flap anchor coupled to upper ends of each of the movable first and second flaps and mounted to the intake tube of the binoculars-shaped valve housing.

* * * * *